(12) United States Patent
Liu et al.

(10) Patent No.: US 11,992,357 B2
(45) Date of Patent: May 28, 2024

(54) TRANSPORT SYSTEM WITH CURVED TRACKS FOR MULTIPLE PULSED X-RAY SOURCE-IN-MOTION TOMOSYNTHESIS IMAGING

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AIXScan Inc., Sunnyvale, CA (US)

( * ) Notice: Subject to any disclaimer, the term of this patent is extended or adjusted under 35 U.S.C. 154(b) by 275 days.

(21) Appl. No.: 17/709,799

(22) Filed: Mar. 31, 2022

(65) Prior Publication Data

US 2022/0313185 A1 Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2024.01)
*A61B 6/02* (2006.01)
(Continued)

(52) U.S. Cl.
CPC .............. *A61B 6/541* (2013.01); *A61B 6/025* (2013.01); *A61B 6/032* (2013.01); *A61B 6/035* (2013.01);
(Continued)

(58) Field of Classification Search
CPC ..... A61B 6/4441; A61B 6/025; A61B 6/4021; A61B 6/502; A61B 6/4275; A61B 6/4476;
(Continued)

(56) References Cited

U.S. PATENT DOCUMENTS 4,716,581 A * 12/1987 Barud .................. A61B 6/4441
378/197
5,550,889 A * 8/1996 Gard ..................... H01J 35/153
378/121
(Continued)

*Primary Examiner* — Irakli Kiknadze
(74) *Attorney, Agent, or Firm* — PatentPC; Bao Tran

(57) ABSTRACT

A transport system with curved track pair is constructed for multiple pulsed X-ray source-in-motion to perform fast digital tomosynthesis imaging. It includes a curved rigid track pair with predetermined curvature, a primary motor stage car loaded with X-ray sources and wheels loaded with tension or compression springs. The car is driven by primary motor mounted at base frame and an engaged gear mounted at the car. The car can carry heavy loads, travel with high precision and high repeatability at all installation orientations while motion vibration is minimal. It is also scalable to have a larger radius. Track angle span usually can be from about ten degrees to about 170 degrees. During imaging acquisition, X-ray sources can sweep precisely from one location to another. The car has enough clearance to move in its path without rubbing wheels on tracks. Better than 0.2 mm overall spatial precision can be achieved with the digital tomosynthesis imaging.

19 Claims, 7 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| *A61B 6/03* | (2006.01) | |
| *A61B 6/04* | (2006.01) | |
| *A61B 6/06* | (2006.01) | |
| *A61B 6/08* | (2006.01) | |
| *A61B 6/40* | (2024.01) | |
| *A61B 6/42* | (2024.01) | |
| *A61B 6/46* | (2024.01) | |
| *A61B 6/58* | (2024.01) | |
| *G01N 23/044* | (2018.01) | |
| *G01N 23/083* | (2018.01) | |
| *G01N 23/18* | (2018.01) | |
| *G06T 7/00* | (2017.01) | |
| *G06T 7/11* | (2017.01) | |
| *G06T 11/00* | (2006.01) | |
| *G06T 17/00* | (2006.01) | |
| *G06V 10/25* | (2022.01) | |
| *G06V 10/62* | (2022.01) | |
| *G16H 10/60* | (2018.01) | |
| *G16H 30/20* | (2018.01) | |
| *G16H 50/20* | (2018.01) | |
| *A61B 6/50* | (2024.01) | |

(52) U.S. Cl.
CPC .............. *A61B 6/0407* (2013.01); *A61B 6/06* (2013.01); *A61B 6/08* (2013.01); *A61B 6/4007* (2013.01); *A61B 6/4014* (2013.01); *A61B 6/4021* (2013.01); *A61B 6/405* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(58) Field of Classification Search
CPC ......... A61B 6/583; A61B 6/467; A61B 6/032; A61B 6/54; A61B 6/4452; A61B 6/06; A61B 6/405; A61B 6/482; A61B 6/4007; A61B 6/4283; A61B 6/4208; A61B 6/4482; A61B 6/4405; A61B 6/035; A61B 6/4014; A61B 6/541; A61B 6/08; A61B 6/0407; A61B 6/56; A61B 6/542; A61B 6/51; A61B 6/584; A61B 6/4241; A61B 6/425; A61B 6/5252; A61B 6/582; A61B 6/466; A61B 2090/3966; A61B 6/512; A61B 6/4417; A61B 6/547; A61B 5/0066; A61B 8/4416; A61B 6/587; A61B 6/4233; A61B 6/4435; A61B 6/107; A61B 6/5205; A61B 6/463; A61B 6/105; A61B 6/4464; G16H 10/60; G16H 40/63; G16H 30/20; G16H 50/20; G06T 17/00; G06T 7/0012; G06T 7/11; G06T 2207/20084; G06T 2207/20081; G06T 2207/10076; G06T 2207/30168; G06T 11/005; G06T 11/006; G06T 7/0016; G06T 11/003; G06T 2207/30096; G06T 2211/436; G06T 2207/30064; G06T 2210/41; G06T 2200/24; G06T 2207/10081; G06T 2211/412; G06T 15/08; G06T 15/005; G06T 2200/04; G06T 2207/10116; G06T 2207/30036; G01N 23/18; G01N 23/083; G01N 23/044; G01N 2223/401; G06V 10/25; G06V 10/62; G06V 10/12; G06V 2201/032; G06V 2201/03; A61L 31/026; A61L 31/18
USPC ........................ 378/4, 9, 193, 196
See application file for complete search history.

(56) References Cited

U.S. PATENT DOCUMENTS

| | | | | |
|---|---|---|---|---|
| 8,094,773 | B2 * | 1/2012 | Boese | A61B 6/025 378/4 |
| 8,559,591 | B2 * | 10/2013 | Boese | A61B 6/4014 378/9 |
| 2002/0190492 | A1 * | 12/2002 | Strong | B60G 3/14 280/124.128 |
| 2004/0109529 | A1 * | 6/2004 | Eberhard | A61B 6/4028 378/23 |
| 2008/0285711 | A1 * | 11/2008 | Avinash | G16H 30/20 378/22 |
| 2010/0091940 | A1 * | 4/2010 | Ludwig | A61B 6/4028 378/22 |
| 2012/0008735 | A1 * | 1/2012 | Maurer | A61B 6/488 378/5 |
| 2012/0189094 | A1 * | 7/2012 | Neushul | A61B 6/035 378/19 |
| 2012/0195403 | A1 * | 8/2012 | Vedantham | A61B 6/022 378/62 |
| 2012/0300901 | A1 * | 11/2012 | Lewalter | H01J 35/13 378/126 |
| 2015/0043712 | A1 * | 2/2015 | Wang | A61B 6/4021 378/42 |
| 2015/0320371 | A1 * | 11/2015 | Heath | A61B 6/542 378/21 |
| 2018/0263578 | A1 * | 9/2018 | Abramovich | A61B 6/4452 |
| 2018/0298970 | A1 * | 10/2018 | Daugirdas | A61B 6/4476 |
| 2019/0126070 | A1 * | 5/2019 | Hsieh | A61B 6/461 |
| 2019/0175131 | A1 * | 6/2019 | Duewer | A61B 6/5205 |
| 2020/0046311 | A1 * | 2/2020 | Vogelsang | A61B 6/582 |

(56) References Cited

U.S. PATENT DOCUMENTS

2020/0305809 A1* 10/2020 Schwoebel ............ H01J 35/147
2020/0352530 A1* 11/2020 Inglese .................. A61B 6/025
2021/0177371 A1* 6/2021 Wang ..................... A61B 90/39
2022/0142591 A1* 5/2022 Zhou ...................... A61B 6/025

* cited by examiner

TRANSPORT SYSTEM WITH CURVED TRACKS FOR MULTIPLE PULSED X-RAY SOURCE-IN-MOTION TOMOSYNTHESIS IMAGING

The present invention claims priority to Provisional Application Ser. Nos. 63/182,426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

The present disclosure relates to a mechanical device for controlled moving at curved trajectory of individually controllable transport of X-ray sources for X-ray imaging exposure, particularly to motion mechanisms of multiple X-ray source fast tomosynthesis imaging system.

BACKGROUND

Tomosynthesis, also digital tomosynthesis (DTS), performs high-resolution limited-angle tomography at radiation dose levels comparable with projection radiography. It has been studied for a variety of clinical applications, including vascular imaging, dental imaging, orthopedic imaging, mammographic imaging, musculoskeletal imaging, and lung imaging. In order to obtain high-quality X-ray images, high precision of spatial dimension is required. In this case, an X-ray source would need to travel around an object with a fan-shape trajectory. For fast imaging also requires higher speed. Source to object distance can go beyond 1000 meters for the larger object, while spatial location accuracy better than 0.4 mm is desirable. There are some prior arts to move X-ray sources around the object in a curved trajectory. However, there are disadvantages to the prior arts. The first disadvantage is poor accuracy. Prior art usually uses a single motor with a long arm to sweep. However, precision is not good enough; it will get worse if the speed is higher or the load is heavier. Usually, there is about 0.0005" or 0.012 mm of bearing clearance. If the bearings are used with 1000 mm arm, it will result in about 12 mm uncertainty. Therefore, a single motor shaft with a long arm would result in very poor spatial accuracy. The second disadvantage is lower speed. Because of poor accuracy, the long arm has to run slowly to avoid vibrations. Lower moving speed limits the speed performance of imaging. That is why it would take quite some time to acquire a complete set of data. The third disadvantage is that it is not very scalable to even longer arm for larger scan objects. For larger objects, the motion radius of the X-ray source has to go larger. However, a long arm would mean more spatial inaccuracy, vibration, and even slower overall speed. X-ray sweeping scan requirements determine motion mechanism. In the high speed tomosynthesis imaging application, tracks must be must be curved and must be in pairs in order to be moving stably in the same rotation plane. The tracks must be able to carry heavy loads with minimum oscillation during load moving. The track should support high speed motion. Tracks must also be scalable with lower cost. The tracks must have high precision with support of all orientations. Therefore, wheels on tracks must be spring pressed so that load will not fall apart. Curve trajectory can be arbitrary, part of circle, ellipse, hyperbola or parabola trajectory are all possible trajectories.

SUMMARY

A transport system with curved track pairs is constructed for multiple pulsed X-ray source-in-motion to perform fast digital tomosynthesis imaging. It includes a transport double-curved rigid tracks with a predetermined radius and a curved car with multiple spring compressed wheel pairs at one or both tracks. Tracks are in the same plane. Wheels are in pairs, and one side or both sides of wheels are spring pressed. Motion is achieved by an engaged curved gear mounted at the car and a motor mounted at the base frame.

Advantages of the system may include one or more of the following. The car can carry heavy loads, travel with high precision, and be repeatable at all orientations and with minimal vibration. The car is driven by a primary motor mounted at the base support frame structure and an engaged curved gear mounted at the primary motor stage car. It is also scalable to a larger radius. When X-ray sources are mounted at the transport system, the X-ray source can sweep precisely from one location to another. Better than 0.2 mm spatial precision can be achieved.

Compared with a single motor-long sweeping arm in prior arts, other advantages may include one or more of the following. One advantage is that it is precise. Better than 0.2 mm overall space precision can be achieved from the prototype system level. Another advantage is that it can carry a heavy load at prototype system test. X-ray sources can usually go from several kilograms to tens of kilograms. Yet a further advantage is that it can also achieve higher speed with much less vibration at the fan-shape trajectory and a stable path of a single X-Y plane. The fourth advantage is that the precision is scalable to a larger sweeping radius. For much larger machines, spatial precision is still the same.

DETAILED DESCRIPTION

Figure 1:
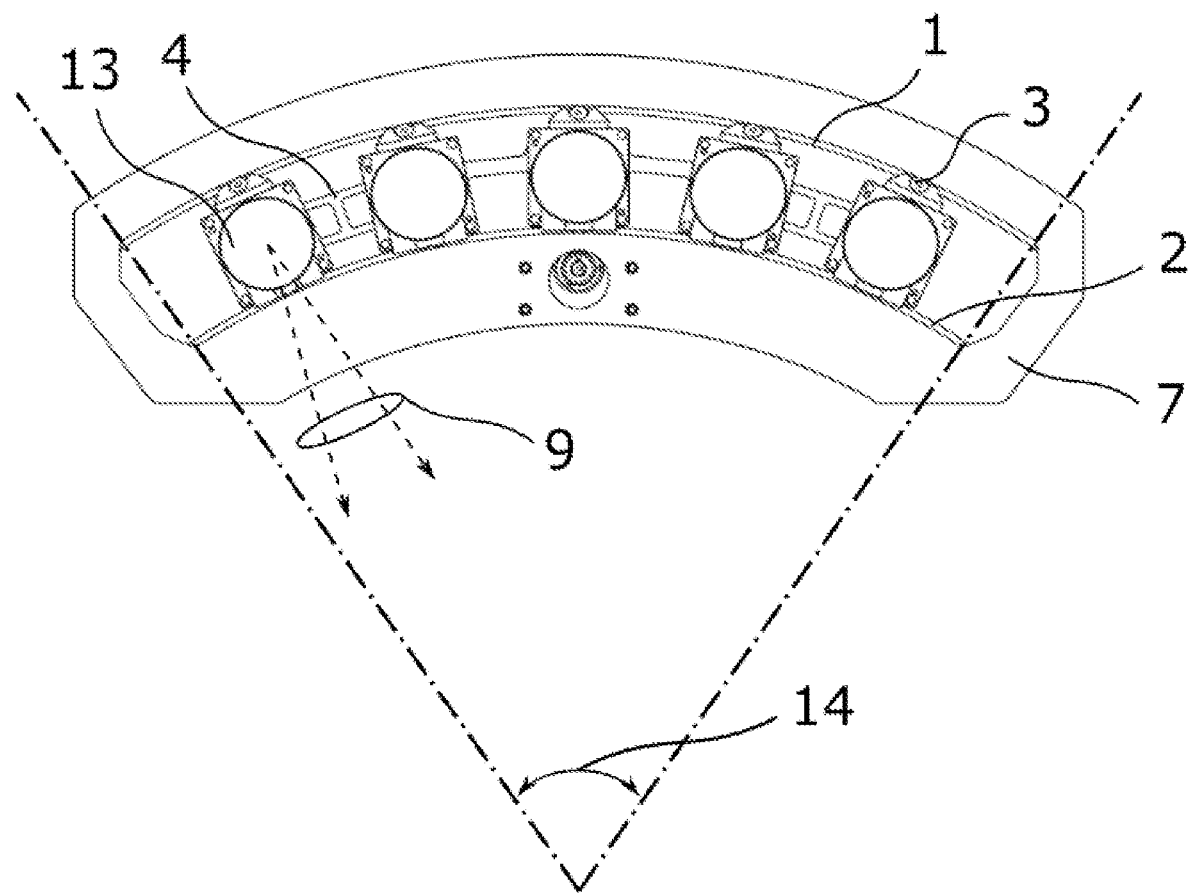
FIG. 1 illustrates an exemplary transport system with single-sided curved track pair for multiple pulsed X-ray source-in-motion tomosynthesis imaging.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

A transport system with a curved track for X-ray source-in-motion to perform fast digital tomosynthesis imaging comprises a pair of curved tracks with either up-and-down or side-by-side configuration, wheels 3, various fastening springs, a primary motor stage car 4 loaded with multiple X-ray sources 13. In the series of inventions, the term of X-ray source-in-motion means that multiple pulsed X-ray sources 13 are sitting in primary motor stage car 4, powered by an electrical primary motor, moving along with primary motor stage car 4 and producing X-ray radiation for imaging while primary motor stage car 4 is moving. The primary motor stage car 4 is driven by a primary motor. Curved track pairs can be either up-and-down or side-by-side arranged. If curved track pair is up-and-down arranged then curved track pair is in the same plane. They are upper track 1 and lower track 2. If curved track pair is side-by-side arranged then planes of curved side-by-side track 8 are parallel. Curvature can be arbitrary. For example, track trajectories with part of circle, ellipse, hyperbola or parabola are all OK. Springs can be compression springs 5, rotation springs 6 or equivalent. The tracks can be either single-sided or double-sided. If tracks are single-sided then usually compression springs 5 are used on wheels 3. If tracks are double-sided then usually rotation springs 6 or equivalent are loaded on wheels 3.

FIG. 1 illustrates an exemplary transport system with the curved track pair for a multiple pulsed X-ray source-in-motion tomosynthesis imaging. Track support frame structure 7 is made of a single-piece hard metal plate. After removing the middle part of the metal plate, it will generate two tracks at cutting edges. One is upper track 1, and the other is lower track 2. In other words, tracks are embedded as part of the track support frame structure 7. The upper track 1 and lower track 2 are in the same plane. The upper track 1 has a larger average radius, while the lower track 2 has a smaller average radius. For each track, there are two surfaces on each track for wheels 3 to contact. Primary motor itself is not shown in FIG. 1 but four mounting screw holes for primary motor are shown.

The transport system is constructed with multiple pulsed X-ray sources-in-motion to perform fast digital tomosynthesis imaging. It includes a transport double-curved nearly concentric rigid tracks with a predetermined radius and a curved primary motor stage car 4 with multiple spring-compressed wheel 3 pairs at each track. The primary motor stage car 4 can carry heavy loads travel with high precision, and repeatability at all orientations and vibration is minimal. The springs here are compression spring 5. The loads include multiple X-ray sources 13. The primary motor stage car 4 is driven by a primary motor mounted at the base frame and an engaged curved gear mounted at the primary motor stage car 4. The drive motor is connected to the drive shaft, which is also coupled to the pinion gear that engages with the gear. The pinion gear is mounted on a drive shaft, and the drive motor is connected to this drive shaft. The other end of the car is equipped with additional pinion gears that engage with the adjacent track. The tracks are connected to a transport frame on two sides of the track by wheels 3. The track can have wheels 3 at each end and has gear teeth on both sides. Wheels 3 are mounted with springs; this helps to keep wheels 3 in contact with tracks securely at all times. A curved gear is mounted at the end of the car and engaged to another gear tooth attached to the wheel mounted on the track. The gears should engage when the primary motor stage car 4 travels on the track. the primary motor can control the primary motor stage car 4 travel direction and how fast it travels when the X-ray source 13 are mounted at the transport system.

As shown in FIG. 1, the primary motor stage car 4 is rigidly mounted on the track base support frame structure 7. At the track base support frame structure 7 there are a first curved track or outer track or upper track 1 and a second curved track or inner track or lower track 2 with each of the tracks having a predetermined radius of curvature. A centerline is a tangent to the curvature of the tracks at one end of the first curved track. The primary motor stage car 4 is configured to travel on the tracks such that a top portion of the car follows the centerline when the primary motor stage car 4 is moved along the tracks. In this embodiment, the primary motor stage car 4 has a number of wheels 3 engaged by corresponding pairs of gears rotated by the motor. In this configuration, track angle span 14 can easily reach beyond 90 degrees for fast digital tomosynthesis imaging. X-ray image quality will get better when coverage of track angle span 14 increases because object 11 can be viewed from more different angles.

The tracks are constructed with a predetermined curvature. Multiple wheels 3 pairs are attached at each track with a compression spring 5 where all-wheel pairs can rotate independently. A circular platform is mounted at each wheel pair with independent motor drive for rotation carriage with X-ray source 13 mounted is moving along tracks with constant speed by engaged gear driven by a primary motor. An elevation motor is driving a circular platform for rotation. The transport system with curved tracks is constructed for multiple pulsed X-ray sources-in-motion to perform fast digital tomosynthesis imaging. It includes a transport double-curved rigid tracks with a predetermined radius and a curved car with multiple springs compressed wheel pairs. The primary motor stage car 4 can carry heavy loads travel with high precision at each track, and repeatability at all orientations and vibration is minimal. The primary motor stage car 4 is driven by a motor mounted at the base frame and an engaged curved gear mounted at the primary motor stage car 4. It is also scalable to a larger radius when X-ray sources 13 are mounted at the transport system. X-ray source 13 can sweep precisely from one location to another and better than fraction of mm spatial precision can be achieved.

The placement of the primary motor stage car 4 between the pairs of tracks and multiple spring-compressed wheels on the track pairs with curved walls serves as a stiffener to support spring-loaded wheels and guide them to move. The primary motor stage car 4 can be loaded with a heavy load or an heavy X-ray source 13. It is also necessary that wheels 3 must not come off of track during operation in the current design. This condition is achieved by a flexible wheel spring with a bearing and short moment arm between the bearing centerline. Centerline front car end is mounted with an engaged gear for driving motor, rotates the gear via motor drive shaft. A precision ball screw-driven shaft connects the motor and gear with appropriate pulleys. A low reduction ratio is obtained with sufficient motor torque it is possible to have an over-rotation speed of gear with motor speed. This arrangement makes it possible to have highly precise motion of large radius X-ray source 13 with high speed.

Figure 2:
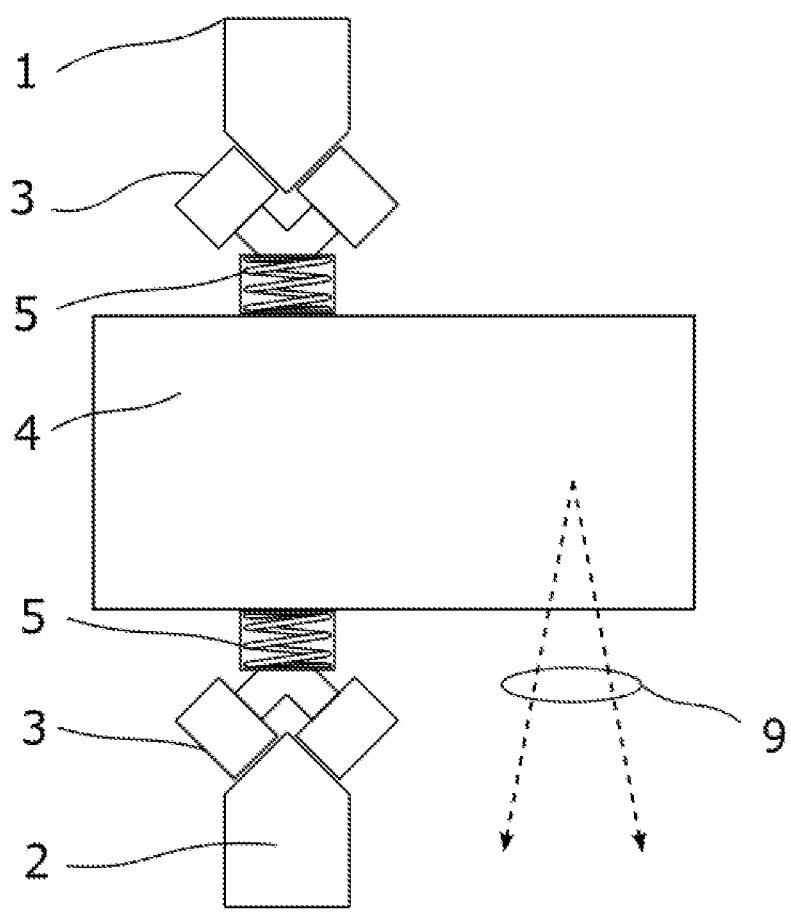
FIG. 2 shows cross section of transport system with pairs of spring-compressed wheels for each X-ray source load at head and feet location.

FIG. 2 shows cross section of two exemplary pairs of spring-compressed wheels for each X-ray source 13 at head and feet location. There are two exemplary pairs of spring compressed wheels 3 for the X-ray sources 13 at the head and feet location. A single primary motor stage car 4 can move freely along the upper track 1 and lower track 2 using spring compressed metal wheel pairs. The primary motor stage car 4 is also a curved single nearly concentric metal piece that can carry heavy loads. In this case, loads are multiple X-ray sources 13 with the same spacing to the adjacent source. For each load, its head and feet are all mounted with wheel 3 pairs. Wheel 3 contact to track surface is line contact, not a point contact for stability and durability purpose.

The primary motor is mounted on the stationary base support frame structure 7. When the motor is turned on, a drive gear coupled to the motor's output shaft to rotate the shaft, causing the primary motor stage car 4 to move along the curved track in the direction controlled by primary motor. Spring-loaded against a biasing spring also keep the primary motor stage car 4 from moving away from the track. The diameter of the curved track is chosen such that it can accommodate primary motor stage car 4 as it travels around an object to be imaged. The transport system comprises curved rigid tracks, wheels, springs, a primary motor stage car and a primary motor. Two concentric single-sided curved tracks are constructed. Each curved track has predetermined radius with primary motor stage car 4. Multiple spring compressed wheels pairs at each track is placed on top of the two concentric curved tracks. When the engaged gear is rotating, the primary motor stage car 4 is driving along the curved tracks. The motor is mounted at the base support frame structure 7, and engage with curved gear mounted at the primary motor stage car 4. Scaling is also possible by simply choosing a larger or smaller radius for the tracks.

A first wheel pair and a second wheel pair are attached at one end to the metal piece. These two-wheel pairs are installed at parallel sides to have space between two single motors installed at both ends of the base frame with the shaft extending upward. They are rotated by electric power from outside to move two attached gears attached to wheels. A single primary motor is also attached to gear to drive attached wheel pair to move forward or backward along track. Another single motor is attached to gear to drive the attached wheel pair to move left or right along the track. A carrier or primary motor stage 4 is a platform to support X-ray sources 13 and other instrumentation like lens tables for object support. All gears are engaged on their shafts to their respective motors. The carrier has an extension for X-ray tubes position that can be adjusted by sliding the extension up and down to compensate for the offset error. As the X-ray source 13 moves, its rotation angle can be measured by an attached angle measuring device mounted on the X-ray source 13.

Track pair that are mounted at base support frame structure must be in a single rigid plane in order to generate good X-ray images. Because all the wheels 3 are spring compressed or tensioned, there will be a significant force on the outer and inner track. Therefore, enforcement is necessary to prevent from being warped. Track enforcement elements are rigid metal pieces spanned from the outer part of the track metal frame to the inner track frame.

Multiple X-ray sources 13 can be mounted on a primary motor stage car 4 at the base support frame structure. These X-ray sources 13 can be pulsed sources with at least one X-ray detector 12 that can be placed in a region for imaging. An X-ray source-in-motion image can be reconstructed based on data from X-ray detector 12. The base support frame structure 7 can be constructed with precision gears, and the primary motor can drive wheels through gear and shaft. Multiple springs pressed wheels pairs and tracks themselves can be made of hard steel while primary motor stage car 4 itself can be made of carbon fiber, aluminum alloy or other lightweight material. The primary motor stage car 4 can also have high-density foam inside to protect X-ray sources 13. The primary motor will have engaged gear that can drive a shaft to slide along track shaft can drive wheels. The movement of the primary motor stage car 4 is highly precise and highly repeatable between the primary motor stage car 4 with minimum and X-ray detector 12 with minimum vibration in order to have a super accurate spatial location during data acquisition.

Figure 3:
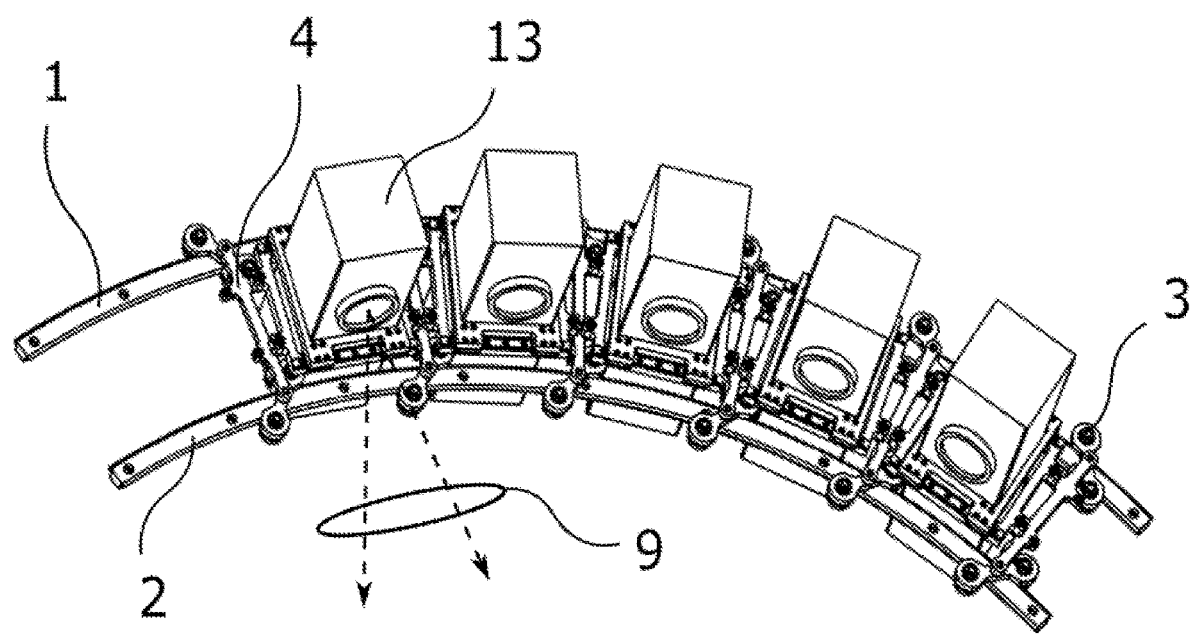
FIG. 3 illustrates an exemplary transport system with double-side curved track pair for multiple pulsed X-ray source-in-motion tomosynthesis imaging.

FIG. 3 shows multiple pulsed X-ray source-in-motion system with double-sided track and wheels secured with rotational springs or equivalent. There are curved gear teeth mounted at the car. The primary motor is mounted at the track base support frame structure. So, motor can control moving speed and moving direction of the primary motor stage car. The primary motor stage car's motion is always in the same plane as that of the track base support frame structure and not sensitive to the location of the center of mass of the load. So, motion is very stable, even when the radius gets larger.

Curved gear teeth and curved tracks are arranged to be engaged and run nearly concentrically. A rotating frame carries a rotary stage that includes loads of X-ray sources 13. The X-ray source 13 can rotate freely and sweep from one side to other side. One end of a motor is attached to the support frame structure and has one or more axles that engage with corresponding curved gear teeth. The other end of the motor may be attached to a threaded shaft that runs through a hole in the rotary stage.

Motor and engaging gear is at base support frame structure with holes is connected to the center of the base frame and has a pin extending inwards curved rigid track is attached to rotating support with screws. At the center of the curved rigid track, there is a hole for the pin to pass through the outer surface of the curved rigid track has to groove for holding car has several wheels 3. In a preferred embodiment, wheels 3 are secured on springs with the center ball rotating in both directions, primary motor stage car 4 is mounted with spring which has tensioner and washer spring can expand and contract lengthwise to change tension for the very high precision device the distance between wheels on each track must be constant.

The advantage of using such a transport system is that there is minimal distortion in the projected images. Actual imaging angle span is typically related to the diameter of the largest item in the scanned region and track angle span 14. Smaller values may be used for tighter turns and larger values for less constrained applications. A turn may be preferable to reduce the angle span rather than constrain the path of the transporter car or other transport structure to a narrow path. A transport system with reduced spatial resolution at the turns uses a high-speed transport system that can traverse a curved path. Another advantage is that upper track 1 and lower track 2 are separate from support frame structure, and upper track 1 and lower track 2 can be mounted to a support frame structure with lighter rigid material like aluminum alloy or carbon fiber composite material.

Figure 4:
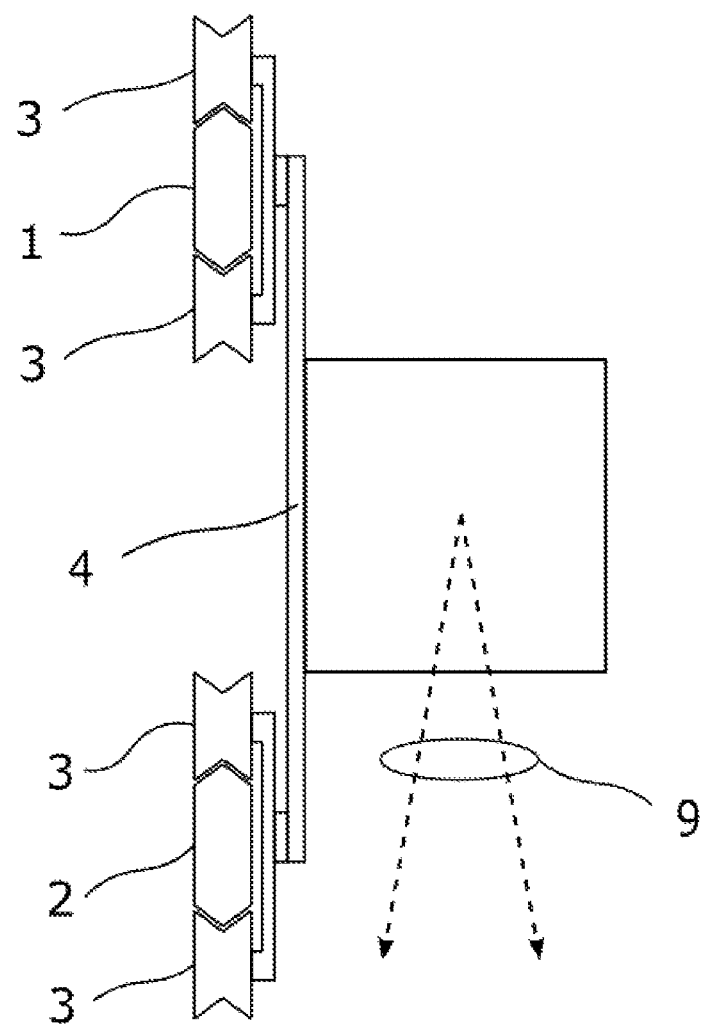
FIG. 4 shows cross section of transport system with two pairs of spring-compressed wheels using double-sided track pair.

FIG. 4 shows cross section of transport system with up-and-down double-side curved track pair. Track base support frame structure and the primary motor stage car of the transport system are arranged concentrically with radius at an angle from horizontal or normal to the preferably base frame. The primary motor stage car 4 is designed with higher rigidity to ensure smooth motion of the primary motor stage car 4. Wheel 3 pairs are arranged along the circular track for support. The angle separates each wheel pair in the plane, and the rolling direction of wheels is opposite to each other. Wheels have diameter wheels spring-loaded with constant spring such that there is enough clearance between track and primary motor stage car. This allows freedom of the primary motor stage car 4 to move around the track in a yawing manner. X-ray beam 9 can be towards down-wards so patient laid down. In this case, cross section shows that the curved track is a double-sided track also with upper track 1 and lower track 2.

Rotational spring 6 or equivalent rotation spring is used. In this configuration, the rigidity requirement of support frame structure is much lower. Rotational spring 6 only apply pressure to double-sided track only, not to support frame structure. Therefore, light metal material or even carbon fiber can be used to build support frame structure.

Figure 5:
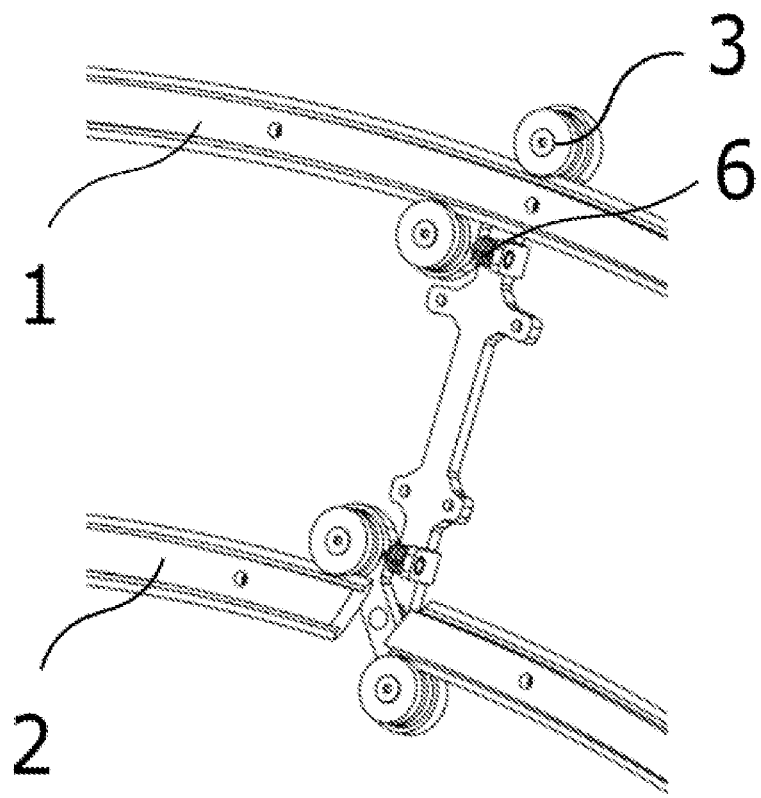
FIG. 5 shows wheels in transport system with fastening from rotation equivalent tension springs.

FIG. 5 shows double sided track rather than single sided track is used to improve stability. Double-sided track use specially manufactured specially polished hard metal, and screw mounted to the support frame structure. While support frame structure can use light metal like aluminum alloy or even carbon fiber composite material. Therefore, machining cost can be lower. Tracks can be easily machine to arbitrary curve. Wheels 3 can be connected together to become primary motor stage car 4 to carry heavy load of X-ray sources 13. One advantage of double-sided track is that it can easily support all orientations like vertical or horizontal configuration.

X-ray beam 9 can also be horizontal oriented so patient just stands up to scan without laying down on the bed. Tracks and wheel can be all standard part to have lower cost. Curved track can cover a wider angle. Track is polished to be smoother, long-life time. Vibration during motion is minimal.

The endpoints of each curve form an imaginary line in the same plane. These two tracks can be regarded as concentric circles or as a straight line. The width of the track depends on the application. With pairs of wheels on each track, each wheel has a different diameter to balance the car. There are multiple wheels pairs for precise speed adjustment and stability. Its task determines the wheel diameter; it should be small enough to carry a heavy load and big enough to reduce rotational inertia wheels should be pressed against the track by springs to prevent slipping.

Figure 6:
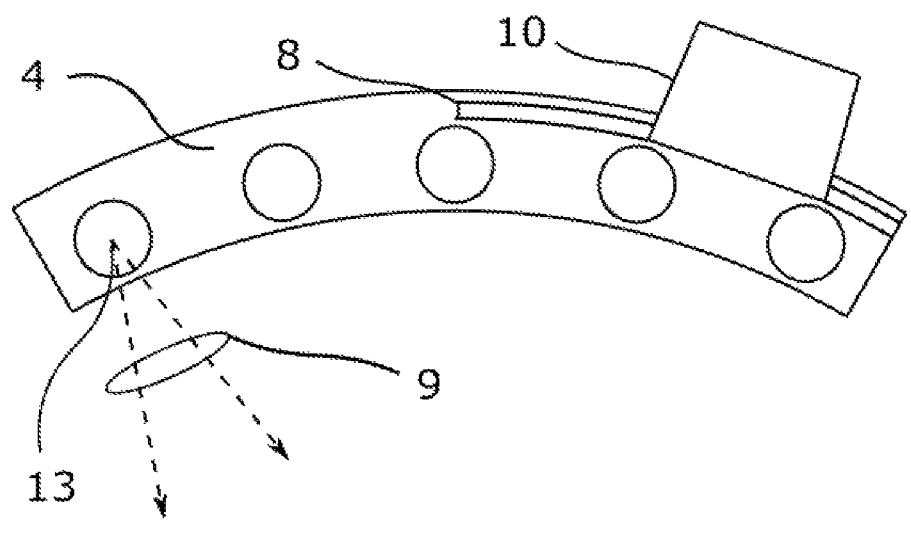
FIG. 6 illustrates an exemplary transport system with side-by-side double-side curved track pair for multiple pulsed X-ray source-in-motion tomosynthesis imaging.
Figure 6:
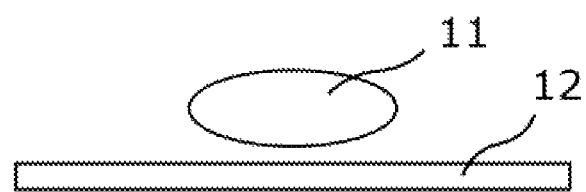

In an embodiment with the same functionality, FIG. 6 illustrates an exemplary transport system with side-by-side double-side curved tracks for a multiple pulsed X-ray source-in-motion tomosynthesis imaging. In this embodiment, curved track pair are double-sided with side-by-side configuration. One of advantages is that tracks are much shorter, numbers of wheels needed are much less and so cost is even lower. Machines with this configuration can be more popular when unit price goes lower. This configuration allows machine to be more modular because primary motor stage car 4 is detachable. Therefore, in this X-ray tomosynthesis imaging system, Primary motor stage car 4, wheel support frame structure 10, a scan object 11 and X-ray detector 12 are all independent elements to each other. Double-sided side-by-side tracks 8 can start using track angle span 14 of about ten degrees to do useful X-ray imaging scan, X-ray beam 9 are towards rotation center where a scan object 11 is located. It is easier to install and uninstall whole system. Compared with other configuration, it is also easier to shield X-ray radiation and easier to do X-ray beam 9 collimation.

Figure 7:
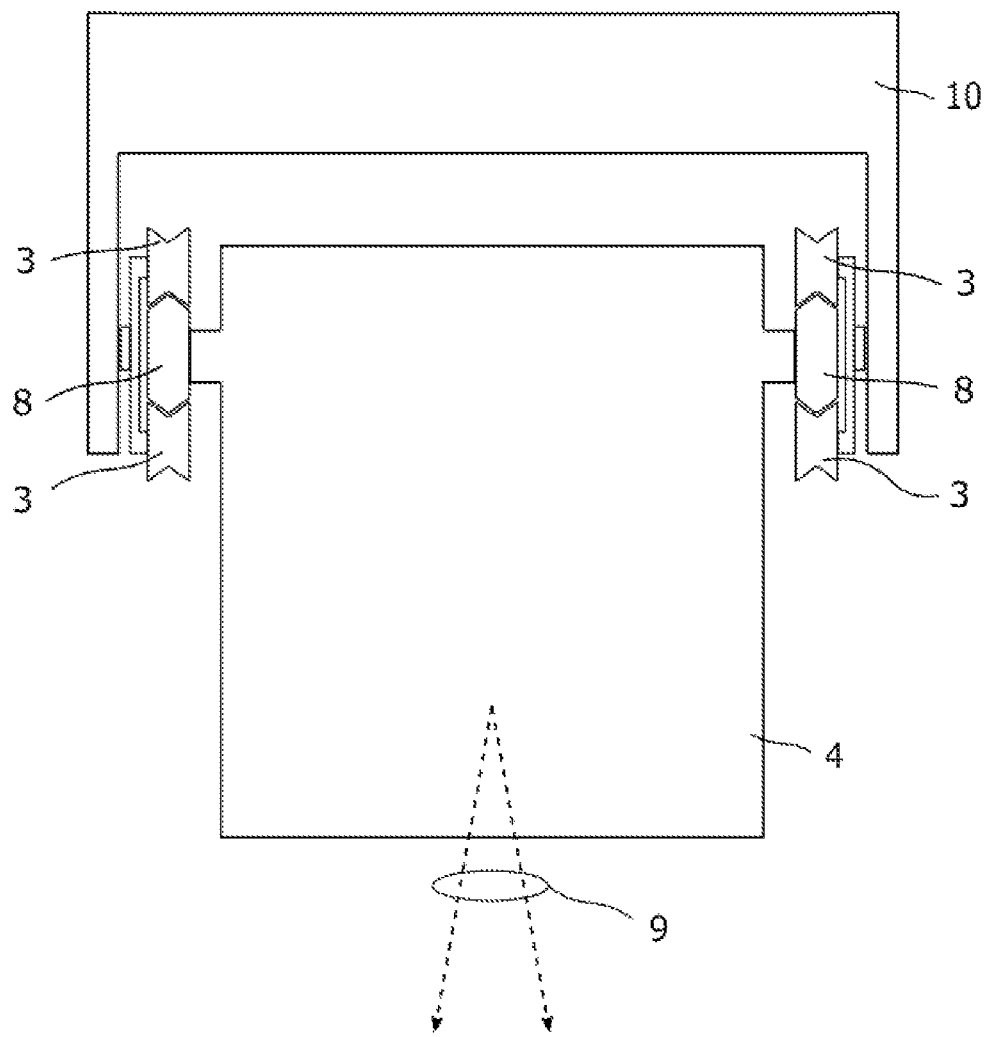
FIG. 7 shows cross section of transport system with side-by-side double-side curved track pair.

FIG. 7 shows cross section of transport system with side-by-side double-side curved track pair. The double-sided tracks are on constructed at body of primary motor stage car 4 while wheels 3 with rotational springs 6 or equivalent are built at stationary wheel support frame structure 10. In other words, in this case, primary motor stage car 4 has no wheels 3 on itself, all wheels 3 are located at stationary wheel support frame structure 10. In this case, cross section shows that the curved tracks are a pair of double-sided side-by-side tracks 8.

Heavy X-ray source 13 load on primary motor stage car 4 is located between track pairs to be stable just like a high-speed train. This configuration would have even more advantages. There are more precise back and forth movement, more repeatable and accurate spatial location, higher speed, lower cost and less vibration. System is easier to maintain, easier to assemble and easier to debug whole system.

Various modifications and alterations of the invention will become apparent to those skilled in the art without departing from the spirit and scope of the invention, which is defined by the accompanying claims. It should be noted that steps recited in any method claims below do not necessarily need to be performed in the order they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Although the invention is described above in terms of various exemplary embodiments and implementations, it should be understood that the various features, aspects, and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

The presence of broadening words and phrases such as "one or more," "at least," "but not limited to" or other such phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A transport system for an X-ray source, comprising:
   a support frame structure to support moving and non-moving mechanical loads;
   a curved concentric track pair with a pre-determined curvature and sweeping angle spanning from 10 degrees to 170 degrees for multiple pulsed X-ray source-in-motion tomosynthesis imaging;
   a curved primary motor stage car loaded with a plurality of X-ray sources mounted on the curved primary motor stage to concentrically aim at an object and actuated by a primary motor coupled to the support frame structure; and
   a plurality of spring-compressed wheels that roll freely along the curved track pair.

2. The system of claim 1, wherein the curved track pair is either single-sided or double-sided.

3. The system of claim 1, wherein trajectory of curved track comprises a curve shape on-demand.

4. The system of claim 1, wherein the curved track pair is planar.

5. The system of claim 1, wherein the plane of a first curved track of the curved track pair is parallel to the plane of a second curved track.

6. The system of claim 1, wherein each X-ray source comprises a head and one or more feet mounted with wheel pairs.

7. The system of claim 1, wherein a motion of the car is planar to a track base structure and insensitive to a location of a center of mass of an X-ray source.

8. The system of claim 1, comprising a plurality of track enforcement pieces that prevent warpage of the inner and outer track of the track frame.

9. The system of claim 1, wherein the primary motor stage car comprises a curved single concentric metal piece.

10. The system of claim 1, wherein the wheel comprises either a compression spring or a rotational spring.

11. The system of claim 1, comprising:
    a plurality of X-ray sources each mounted at the primary motor stage;
    a supporting frame structure that provides housing for the primary motor stage; and
    an X-ray flat panel detector to receive X-ray and transmit X-ray imaging data.

12. The system of claim 1, comprising a double sided track where wheels are coupled to both sides of the double sided track to carry a predetermined load with a vertical or horizontal configuration.

13. The system of claim 1, wherein one or more of the X-ray sources is activated using a predetermined scheme.

14. The system of claim 1, wherein an initial spatial position of the primary motor stage is adjustable by software.

15. The system of claim 1, wherein a result of each and accumulated analysis determines the next X-ray source and exposure condition.

16. The system of claim 1, wherein exposure time of X-ray source is adjustable by software.

17. The system of claim 1, wherein the object stands up.

18. The system of claim 1, wherein each X-ray source moves a distance around a static position on X-ray tube target by deflection electrical field or deflection magnetic field.

19. The system of claim 1, wherein each X-ray source has a speed that equals to a group X-ray source speed but an opposite moving direction, the individual X-ray source is triggered through an external exposure control unit, and wherein the X-ray source stays relatively standstill during an X-ray pulse trigger exposure duration.

* * * * *